US009480453B2

(12) United States Patent
Yamanaka et al.

(10) Patent No.: US 9,480,453 B2
(45) Date of Patent: Nov. 1, 2016

(54) X-RAY IMAGING DEVICE

(71) Applicant: THE YOSHIDA DENTAL MFG. CO., LTD., Sumida-ku, Tokyo (JP)

(72) Inventors: Michizo Yamanaka, Tokyo (JP); Terumi Takemoto, Tokyo (JP); Takeshi Tomoe, Tokyo (JP)

(73) Assignee: THE YOSHIDA DENTAL MFG. CO., LTD., Tokyo (JP)

( * ) Notice: Subject to any disclaimer, the term of this patent is extended or adjusted under 35 U.S.C. 154(b) by 62 days.

(21) Appl. No.: 14/438,017

(22) PCT Filed: Oct. 8, 2013

(86) PCT No.: PCT/JP2013/077358
§ 371 (c)(1),
(2) Date: Apr. 23, 2015

(87) PCT Pub. No.: WO2014/069186
PCT Pub. Date: May 8, 2014

(65) Prior Publication Data
US 2015/0289833 A1 Oct. 15, 2015

(30) Foreign Application Priority Data

Nov. 5, 2012 (JP) ................................. 2012-243264

(51) Int. Cl.
*A61B 6/02* (2006.01)
*A61B 6/00* (2006.01)
(Continued)

(52) U.S. Cl.
CPC ................. *A61B 6/54* (2013.01); *A61B 6/027* (2013.01); *A61B 6/035* (2013.01); *A61B 6/14* (2013.01);
(Continued)

(58) Field of Classification Search
USPC ............. 378/4, 11, 15, 20, 39, 87, 195–198, 378/204, 205, 208, 210
See application file for complete search history.

(56) References Cited

U.S. PATENT DOCUMENTS 7,549,799 B2 * 6/2009 Ye ........................... G03B 42/04
378/189
8,300,762 B2 * 10/2012 Suzuki ................... A61B 6/032
378/15
(Continued)

FOREIGN PATENT DOCUMENTS

JP 9-327453 12/1997
JP 10-225455 8/1998
(Continued)

OTHER PUBLICATIONS

International Search Report for PCT/JP2013/077358 mailed Jan. 14, 2014 (4 pages).
(Continued)

*Primary Examiner* — Bernard Souw
(74) *Attorney, Agent, or Firm* — Merchant & Gould P.C.

(57) ABSTRACT

An X-ray imaging device wherein a control section rotates an arcuate movement arm by actuating a turn-driving unit, turns an X-ray source and an X-ray sensor around a subject, and actuates a shifting unit to simultaneously shift the transmission part of the subject, through which an X-ray flux detected by the X-ray sensor passing. Thus provided is an X-ray imaging device in which an X-ray imaging unit having a comparatively narrow detection area can be used to reduce costs, the imaging operation efficiency can be improved, and the vibration of moved members, such as the X-ray imaging unit, can be reduced.

12 Claims, 14 Drawing Sheets

(51) Int. Cl.
  *G01N 23/00* (2006.01)
  *G06T 11/00* (2006.01)
  *A61B 6/03* (2006.01)
  *A61B 6/14* (2006.01)
  *A61B 6/06* (2006.01)

(52) U.S. Cl.
  CPC ........... *A61B 6/4233* (2013.01); *A61B 6/4441* (2013.01); *A61B 6/4476* (2013.01); *A61B 6/5241* (2013.01); *A61B 6/06* (2013.01); *A61B 6/405* (2013.01); *A61B 6/542* (2013.01)

(56) References Cited

U.S. PATENT DOCUMENTS

| | | | | |
|---|---|---|---|---|
| 8,855,262 B2* | 10/2014 | Takemoto | ................ | A61B 6/02 378/197 |
| 8,989,343 B2* | 3/2015 | Arai | .................... | G06T 7/0012 378/20 |
| 2009/0245464 A1* | 10/2009 | Yamaguchi | .......... | A61B 6/5241 378/62 |
| 2010/0246755 A1* | 9/2010 | Suzuki | ................... | A61B 6/032 378/11 |
| 2011/0176717 A1 | 7/2011 | Siren et al. | | |
| 2012/0093284 A1* | 4/2012 | Takemoto | ................ | A61B 6/02 378/19 |
| 2013/0287166 A1* | 10/2013 | Arai | ..................... | G06T 7/0012 378/20 |
| 2013/0294569 A1* | 11/2013 | Yoshikawa | ............ | A61B 6/032 378/4 |

FOREIGN PATENT DOCUMENTS

| | | |
|---|---|---|
| JP | 2006-34670 | 2/2006 |
| WO | WO 2009/063974 | 5/2009 |
| WO | WO 2010/150719 | 12/2010 |
| WO | 2012/088243 A2 | 6/2012 |

OTHER PUBLICATIONS

International Written Opinion for PCT/JP2013/077358 mailed Jan. 14, 2014 (4 pages).
Search Report for European Application No. 13852040.8, mailed May 13, 2016.
Office Action for Japanese Patent Application No. 2012-243264, mailed Jun. 7, 2016.

* cited by examiner

X-RAY IMAGING DEVICE

This application is a U.S. National Stage Application under 35 U.S.C. §371 of International Patent Application No. PCT/JP2013/077358 filed 10 Aug. 2013, which claims the benefit of priority to Japanese Patent Application No. 2012-215624 filed 28 Sep. 2012 and Japanese Patent Application No. 2012-243264 filed 5 Nov. 2012, the disclosures of all of which are hereby incorporated by reference in their entireties. The International Application was published in Japanese on 8 May 2014 as WO 2014/069186.

TECHNICAL FIELD

The present invention relates to an X-ray imaging device, and particularly relates to an X-ray imaging device that obtains CT (computer tomography method) images, using an X-ray imaging unit having a comparatively narrow detection area.

BACKGROUND ART

There is known an X-ray imaging device for dental care that is provided with an X-ray source for irradiating a subject with X-ray flux, an X-ray imaging unit for detecting X-ray flux passing through the subject, and a turn-driving unit for turning the X-ray source and the X-ray imaging unit around the subject, and is capable of CT imaging and panorama imaging (see Patent Literature 1). The X-ray imaging device disclosed by Patent Literature 1 uses a two dimensional sensor having a wide detection area necessary for CT imaging as an X-ray imaging unit.

However, a two dimensional sensor with a wide detection area is so expensive that an X-ray imaging device becomes expensive as a whole. In this situation, an X-ray imaging device is presented that detects X-ray flux passing through a subject, by moving an X-ray imaging unit with a comparatively narrow detection area by a moving unit, and thereby functions as a virtual X-ray imaging unit for a range of the movement (Patent Literature 2).

RELATED ART DOCUMENT

Patent Literature

Patent Literature 1: JP 10-225455 A
Patent Literature 2: WO 2010/150719

DISCLOSURE OF THE INVENTION

Problems to be Solved by the Invention

However, the X-ray imaging device disclosed by Patent Literature 2 needs to repeat execution of, for example, a step of imaging while moving the X-ray imaging unit by the moving unit in a certain range and a step of shift-turning the X-ray source and the X-ray imaging unit around a subject by a turn-driving unit. Consequently, when moved members such as the X-ray imaging unit and the like are temporarily stopped and restarted, it is necessary to decelerate and accelerate these moved members. Consequently, as the moving speed of the X-ray imaging unit is low immediately after the start of a movement and immediately before the stop of the movement of the X-ray imaging unit, resulting in a long total imaging time and a drop of imaging work efficiency. Further, inertia force due to acceleration or deceleration acts on moved members such as the X-ray imaging unit, which also causes the moved members to vibrate.

The present invention has been developed addressing these problems, and an object of the invention is to provide an X-ray imaging device that enables reducing cost, using an X-ray imaging unit with a comparatively narrow detection area, and reducing vibration of moved members such as the X-ray imaging unit.

Means for Solving the Problems

In order to solve the above-described problems, an X-ray imaging device according to the present invention includes: an X-ray source for irradiating a subject with X-ray flux; an X-ray imaging unit for detecting the X-ray flux passing through the subject; a support member for supporting the X-ray source and the X-ray imaging unit; a turn-driving unit for turning the X-ray source and the X-ray imaging unit around the subject by rotating the support member; a shifting unit for shifting a transmission part of the subject, through which the X-ray flux detected by the X-ray imaging unit passing; and a control section for controlling operation of the turn-driving unit and the shifting unit, wherein the control section executes detection of the X-ray flux passing through the subject by the X-ray imaging unit, while simultaneously executing turning of the X-ray source and the X-ray imaging unit around the subject by rotating the support member by operating the turn-driving unit, and shifting the transmission part of the subject, through which the X-ray flux detected by the X-ray imaging unit passing, by operating the shifting unit.

According to this aspect of the invention, by shifting the transmission part of the subject, through which X-ray flux L detected by the X-ray imaging unit passing, the X-ray imaging unit can function as a two dimensional X-ray imaging unit for a virtual wide range in a range corresponding to the shifting of the transmission part. In such a manner, using, for example, an inexpensive X-ray imaging unit having a detection area in a comparatively narrow range, CT images can be obtained, which contribute to reduction in cost.

Further, while simultaneously executing turning of the X-ray source and the X-ray imaging unit around the subject and shifting of the transmission part of the subject, through which X-ray flux detected by the X-ray imaging unit passing, detection of the X-ray flux passing through the subject is executed. Thus, it is possible to reduce temporary stop and restart of moved members such as the X-ray imaging unit. As a result, as it is possible to reduce the decrease in the speed caused by operation of temporal stop and restart of the moved members from the start to end of X-ray imaging, the total imaging time becomes short, and the imaging operation efficiency is improved. Further, as it is possible to decrease acceleration and deceleration acting on the moved members, the inertia force based on the acceleration or deceleration can be decreased so that the vibration of the moved members caused by the inertia force can be decreased and the durability of the moved members can be improved.

That is, by using an X-ray imaging unit having a detection area with a comparatively narrow range, it is possible to reduce the cost, and also provide an X-ray imaging device that enables improvement of the imaging operation efficiency and reduction in vibration of moved members such as the X-ray imaging unit.

In another aspect of the invention, the control section controls operation of the turn-driving unit and the shifting unit such that neighboring transmission parts, through which the X-ray flux passing, contact with each other at both time points before and after the support member is rotated one time.

According to this aspect of the invention, as image data (projection data) necessary for generation of CT images can be effectively obtained, it is possible to further improve the imaging operation efficiency while ensuring image quality.

Still further, in another aspect of the invention, the X-ray imaging device further includes a turning-center-position horizontally moving mechanism for horizontally moving a turning center position of the support member in a direction along a line connecting the X-ray source with the X-ray imaging unit.

According to this aspect of the invention, the distance between the X-ray source and the subject can be varied by the turning-center-position horizontally moving mechanism, and it is thereby possible to adjust the largeness of FOV (field of view).

Yet further, in another aspect of the invention, a slit for restricting a range of X-ray projected from the X-ray source is arranged in order to face the X-ray imaging unit across the subject.

According to this aspect of the invention, by reducing the amount of scattering rays by arranging the slit for restricting the range of X-ray flux, image quality can be improved.

Further, in another aspect of the invention, the shifting unit is an arcuate movement unit for arcuate moving the X-ray imaging unit around the subject in order to rotate the X-ray imaging unit around an arcuate movement central axis arranged on a line connecting the subject with the X-ray imaging unit; the support member comprises an arcuate movement arm that is axially supported around the arcuate movement central axis arranged for a turning arm turned by the turn-driving unit; the arcuate movement unit that arcuately moves the arcuate movement arm is arranged under the turning arm; wherein the X-ray source and the X-ray imaging unit are rotated around the subject by rotating the arcuate movement arm by turning the arcuate movement arm by the turn-driving unit; and the X-ray imaging unit is arcuately moved around the subject by rotating the arcuate movement arm by the arcuate movement unit.

According to this aspect of the invention, the X-ray source and the X-ray unit are arranged at the arcuate movement arm, which is a support member, and the arcuate movement arm is axially supported around the arcuate movement central axis arranged at the turning arm. Thus, the X-ray source and the X-ray imaging unit arranged at the arcuate movement arm can be turned around the subject by the turn-driving unit through the turning arm. Further, by rotating the arcuate movement arm by the arcuate movement unit, the X-ray imaging unit can be arcuately moved around the arcuate movement central axis, and the transmission part of the subject, through which the X-ray flux passing, can be shifted. Accordingly, by detecting the X-ray flux passing through the subject while arcuate movement the X-ray imaging unit by arcuate movement unit, the X-ray imaging unit can function as a two dimensional imaging unit for a virtual wide range in a range of the arcuate movement.

Still further, in another aspect of the invention, the arcuate movement central axis is provided at a position where the X-ray source is arranged.

According to this aspect of the invention, the X-ray imaging unit is arcuately moved with the X-ray source as the center, without arcuately moving the X-ray source, and it is thereby possible to restrict blurring of an image, projecting stabilized X-ray flux. Further, for example, by rotating the X-ray source in the moving direction of the X-ray imaging unit in order to match with the arcuate movement of the X-ray imaging unit, as a constant region of X-ray flux can be projected to an X-ray imaging unit, uniform X-ray flux without variation can be always projected to the subject.

Yet further, in another aspect of the invention, the shifting unit is a turning-center-position circumferential-direction-moving mechanism for moving a turning-center position of the support member along a circumferential direction of a circle having a center at a point on a line connecting the X-ray source with the X-ray imaging unit.

According to this aspect of the invention, the support member at which the X-ray source and the X-ray imaging unit are arranged is turned around the turning center position of the support member by the turn-driving unit, and the turning center position of the support member is moved by the turning-center-position circumferential-direction-moving mechanism along the circumferential direction of a circle with a center at a point on a line connecting the X-ray source with the X-ray imaging unit. Thus, the X-ray imaging unit is arcuately moved around the above-described point, and the transmission part of the subject, through which the X-ray flux passing, can be shifted. Accordingly, by detecting X-ray flux passing through the subject while arcuate movement the X-ray imaging unit by the turning-center-position circumferential-direction-moving mechanism, the X-ray imaging unit can function as a two dimensional imaging unit for a virtual wide range in a range of the arcuate movement.

Further, the shifting unit is a linearly moving unit arranged on the support member to linearly move the X-ray imaging unit.

According to this aspect of the invention, the X-ray imaging unit can be linearly moved by the linearly moving unit and the transmission part of the subject, through which the X-ray flux passing, can be thereby shifted. Accordingly, by detecting X-ray flux passing through the subject while linearly moving the X-ray imaging unit by the linearly moving unit, the X-ray imaging unit can function as a two dimensional imaging unit for a virtual wide range in a range of the linear movement.

Advantages of the Invention

According to the present invention, it is possible to provide an X-ray imaging device that enables reducing cost, using an X-ray imaging unit with a comparatively narrow detection area, and reducing vibration of moved members such as the X-ray imaging unit.

EMBODIMENTS FOR CARRYING OUT THE INVENTION

Figure 1:
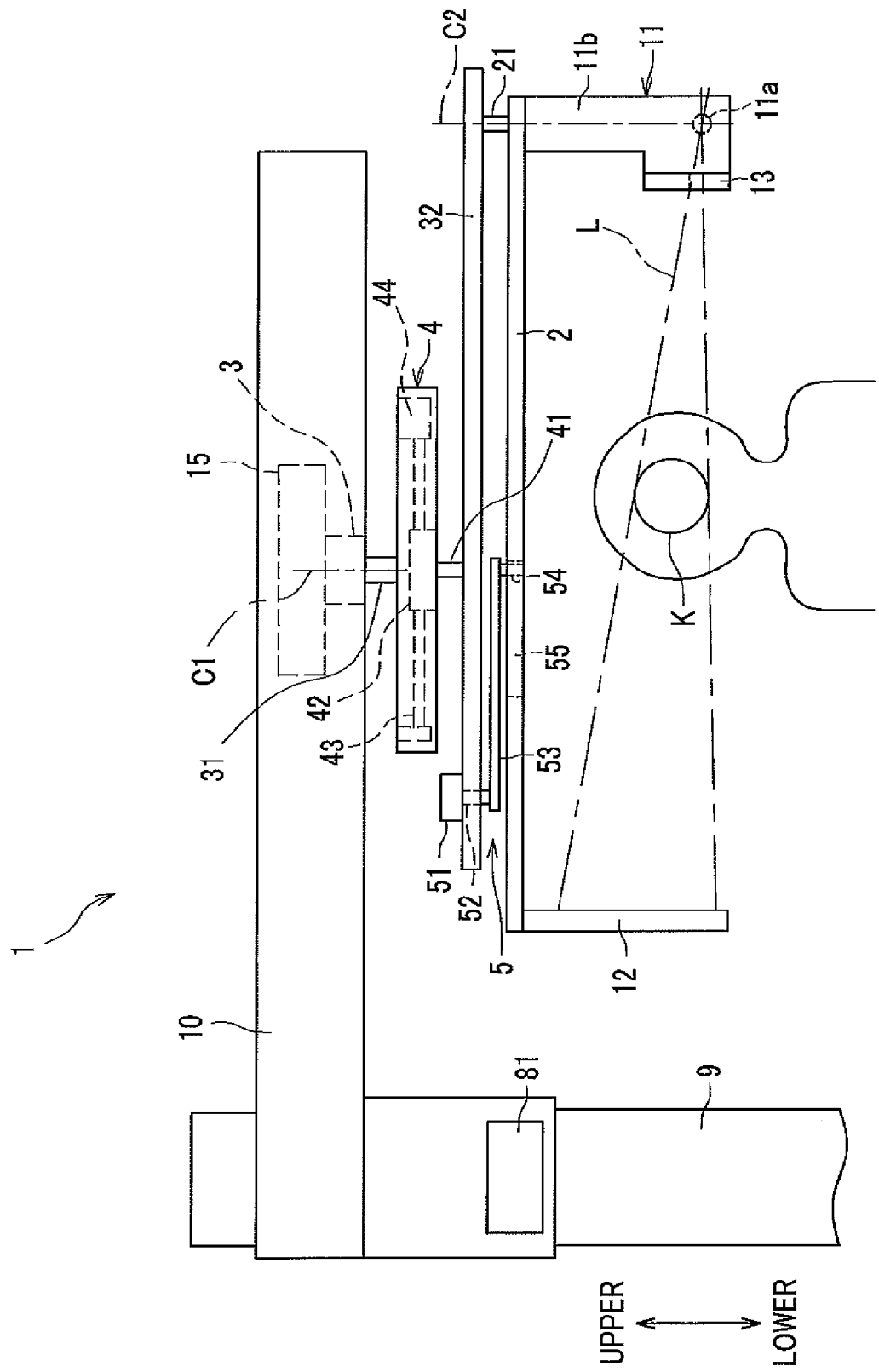
FIG. 1 is a schematic side view of the outline configuration of an X-ray imaging device in a first embodiment according to the present invention.

Embodiments of the present invention will be described in detail, referring to the drawings, as appropriate.

Incidentally, the same reference symbol will be assigned to the same member or members corresponding to each other. Further, the size and the shape of a member may be schematically represented with a change or exaggeration for the convenience of illustration.

First Embodiment

Figure 2:
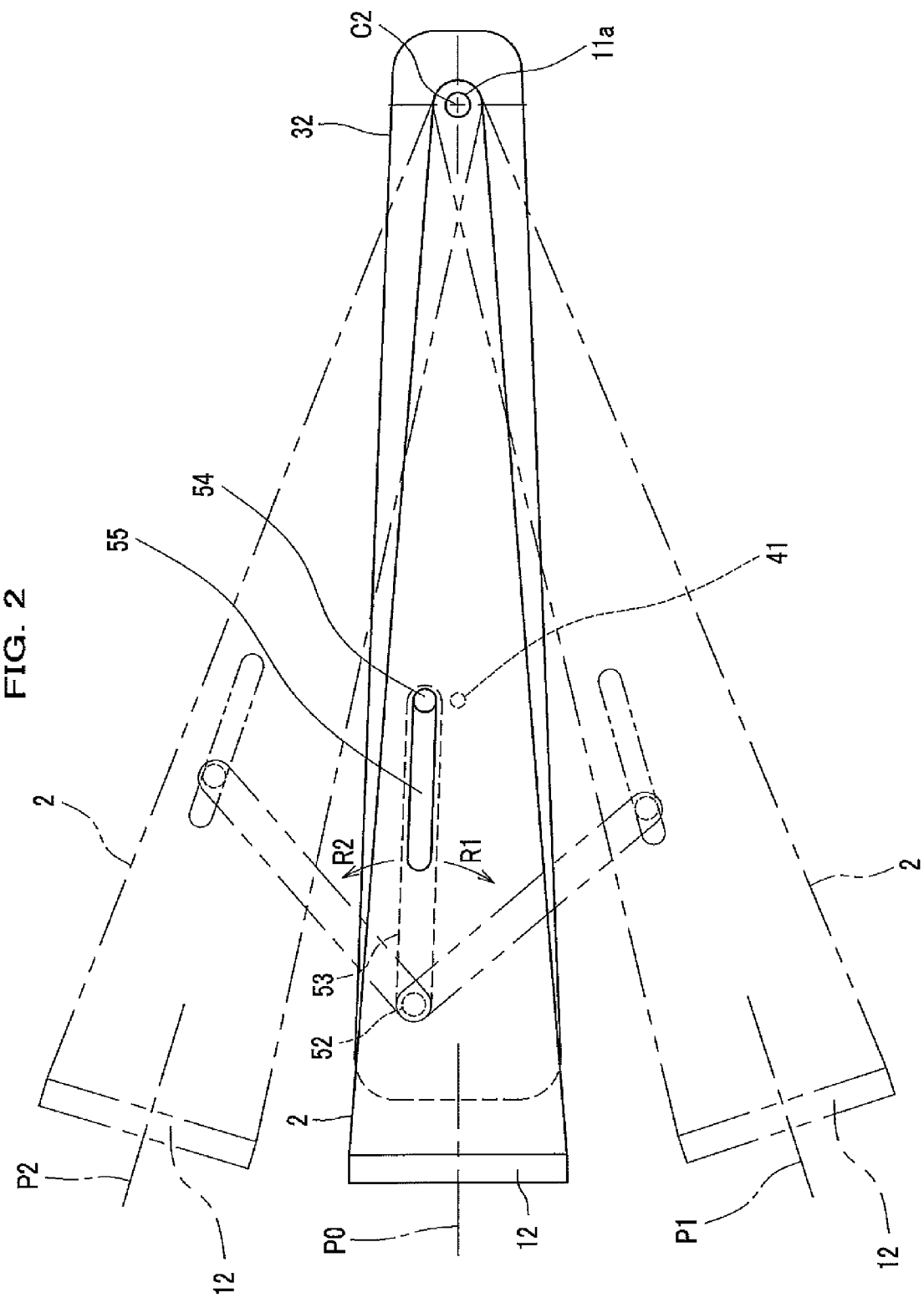
FIG. 2 is a bottom view of the main part for illustration of the operation of a shifting unit.

FIG. 1 is a schematic side view of the outline configuration of an X-ray imaging device 1 in a first embodiment according to the present invention. FIG. 2 is a bottom view of the main part for illustration of the operation of a shifting unit 5.

As shown in FIG. 1, the X-ray imaging device 1 for dentistry in the first embodiment according to the invention is provided with a head 11 having an X-ray source 11a for irradiating a subject K with X-ray flux L, an X-ray sensor 12 as an X-ray imaging unit, an arcuate movement arm 2 as a support member for supporting the X-ray source 11a and the X-ray sensor 12, a turn-driving unit 3 such as a servo motor for rotating the arcuate movement arm 2 around an arm turning central axis C1, and a shifting unit 5 for shifting a transmission part of the subject K, through which the X-ray flux L detected by the X-ray sensor 12 passing.

Incidentally, in the present embodiment, a case of application to dentistry will be described, however, without being limited thereto, a wide variety of applications in the medical field and the like are possible.

The turn-driving unit 3 is installed on an X-Y table 15 and is configured to be able to rotationally drive a turning shaft 31 through a decelerating mechanism, not shown. The turn-driving unit 3 and the turning shaft 31 are movable in a two dimensional plane by the X-Y table 15.

The turn-driving unit 3 and X-Y table 15 are disposed in a frame 10, which horizontally extends, and the frame 10 is supported movably in the upper-lower direction with respect to a post 9, which vertically extends. Symbol 81 in FIG. 1 represents an operating section operated by an operator.

The turning shaft 31 is fixed to the upper portion of a turning-center-position horizontally moving mechanism 4, and the turning-center-position horizontally moving mechanism 4 has a connecting shaft 41 fixed on the upper surface of a turning arm 32.

The turning-center-position horizontally moving mechanism 4 has a function to horizontally move the connecting shaft 41 along the line connecting the X-ray source 11a with the X-ray sensor 12, concretely along the longitudinal direction of the turning arm 32. Herein, the turning-center-position horizontally moving mechanism 4 is provided with a nut section 42 to which the connecting shaft 41 is fixed, a male screw member 43 screw-engaged with the nut section 42, and a male-screw-member rotationally driving unit 44 such as a servo motor that rotationally drives the male screw member 43. That is, in the turning-center-position horizontally moving mechanism 4, the nut section 42 is rotated by the operation of the male-screw-member rotationally driving unit 44, and the connecting shaft 41 can be shifted along the longitudinal direction of the turning arm 32 with respect to the arm turning central axis C1 by screw transfer operation. By such a structure, it is possible to vary the distance between the X-ray source 11a and the subject K, and the size of FOV (the field of view) can be thereby adjusted.

The turn-driving unit 3 has a function to turn the arcuate movement arm 2 through the turning-center-position horizontally moving mechanism 4 and the turning arm 32 so as to rotate the X-ray source 11a and the X-ray sensor 12 around the subject K.

The shifting unit 5 has a function to shift a transmission part of the subject K, through which the X-ray flux L detected by the X-ray sensor 12 passing, substantially perpendicularly to a line connecting the X-ray source 11a with the X-ray sensor 12. In the present embodiment, the shifting unit 5 is an arcuate movement unit for arcuate moving the X-ray sensor 12 around an arcuate movement central axis C2 arranged on a line connecting the subject K with the X-ray sensor 12 to thereby arcuately move the X-ray sensor 12 around the subject K.

With such a structure, the X-ray imaging device 1 turns the turning arm 32 by the turn-driving unit 3 to thereby rotate the arcuate movement arm 2 and thereby rotate the X-ray source 11a and the X-ray sensor 12 around the subject K, and can arcuately move the X-ray sensor 12 by rotating the arcuate movement arm 2 around the subject K by the shifting unit 5.

The X-ray source 11a is arranged at a support member 11b fixed downward from the arcuate movement arm 2. Accordingly, the projection direction of X-ray flux L projected from the X-ray source 11a varies with the rotation of the arcuate movement arm 2, and the X-ray sensor 12 also arcuately moves, in synchronization in order to follow the projection direction of the X-ray flux L (see FIG. 2).

Further, a slit 13 for restricting the range of X-ray flux L projected from the X-ray source 11a is arranged on the subject K side of the head 11 in order to face the X-ray sensor 12 across the subject K. The X-ray flux L having been narrowed by the slit 13 passes through the subject K and is detected by the X-ray sensor 12. By arranging the slit 13, the amount of scattering rays can be reduced so that the image quality can be improved. The slit 13 may be arranged in order to extend downward from the arcuate movement arm 2.

The X-ray sensor 12 can be configured by the use of an image sensor having a vertically longitudinal detection area in a comparatively narrow range, such as a CMOS sensor, a CCD sensor, a CdTe sensor, or the like to detect X-ray flux L passing through the subject K.

For example, CMOS sensors feature low cost and low power consumption. CCD sensors feature a high resolution, and allow selection of an optical image sensor, based on specifications required for an X-ray imaging device.

The arcuate movement arm 2 is axially and rotatably supported around an axial member 21 having the arcuate movement central axis C2 arranged at the turning arm 32 turned by the turn-driving unit 3. The arcuate movement central axis C2 is herein arranged coaxially with the X-ray source 11a of the head 11 arranged at the arcuate movement arm 2. By such a structure, the X-ray sensor 12 is arcuately moved with the X-ray source 11a as the center, without arcuately moving the X-ray source 11a, and it is thereby possible to restrict blurring of an image, projecting stabilized X-ray flux L. Further, for example, by rotating the X-ray source 11a in the moving direction of the X-ray sensor 12 in order to match with the arcuate movement of the X-ray sensor 12, as a constant region of X-ray flux can be projected to an X-ray imaging unit, uniform X-ray flux without variation can be always projected to the subject K.

The arcuate movement arm 2 is provided with the X-ray source 11a, the slit 13, and the X-ray sensor 12 on a line. Thus, it is possible to narrow the X-ray flux L projected from the X-ray source 11a by the slit 13 to project a constant region of the X-ray flux L to the X-ray sensor 12. Accordingly, it is possible to efficiently irradiate the subject K always with a uniform X-ray flux L without variation.

As shown in FIG. 1 and FIG. 2, the shifting unit 5 is provided with a rotating-arm rotationally driving unit 51 such as a servo motor installed at the turning arm 32, a rotation shaft 52 connected to the rotating-arm rotationally driving unit 51, a rotating arm 53 to which one end portion the tip end of the rotation shaft 52 is fixed, a driving pin 54 arranged at the other end portion of the rotating arm 53, and a guide groove 55 formed on the arcuate movement arm 2 in order to engage with the driving pin 54.

With such a structure, when the shifting unit 5 rotates the rotating arm 53 around the rotation shaft 52 clockwise R1 in FIG. 2, the arcuate movement arm 2 arcuately moves around the arcuate movement central axis C2 from a central position P0 to a gradient position P1 in FIG. 2. When the shifting unit 5 rotates likewise the rotating arm 53 around the rotation shaft 52 counterclockwise R2 in FIG. 2, the arcuate movement arm 2 arcuately moves around the arcuate movement central axis C2 from the central position P0 to a gradient position P2 in FIG. 2.

In such a manner, by arcuate movement the arcuate movement arm 2 around the arcuate movement central axis C2, it is possible to arcuately move the slit 13 and the X-ray sensor 12 arranged at the arcuate movement arm 2.

Though not shown, the X-Y table 15 is constructed by combination of a linearly moving guide arranged movably in X-axial direction and a linearly moving guide arrange movably in Y-axial direction, the linearly moving guides being arranged in order to be perpendicular to each other in the horizontal direction.

Being provided with the X-Y table 15, as the X-ray imaging device 1 can translates the arcuate movement arm 2 in a horizontal two dimensional plane, the X-ray imaging device 1 functions as an imaging device capable of generating both CT images and panorama images.

That is, in using the X-ray imaging device 1 as a CT imaging device, the X-Y table 15 is fixed, and the position of the arm rotation central axis C1 in the horizontal plane is thereby fixed, which enables CT imaging. On the other hand, in using the X-ray imaging device 1 as a usual panorama imaging device, in a state that the arcuate movement arm 2 is fixed without being arcuately moved, the arcuate movement arm 2 and the turning arm 32 are integrally translated by the X-Y table 15 in a horizontal two dimensional plane, which enables panorama imaging.

Figure 3:
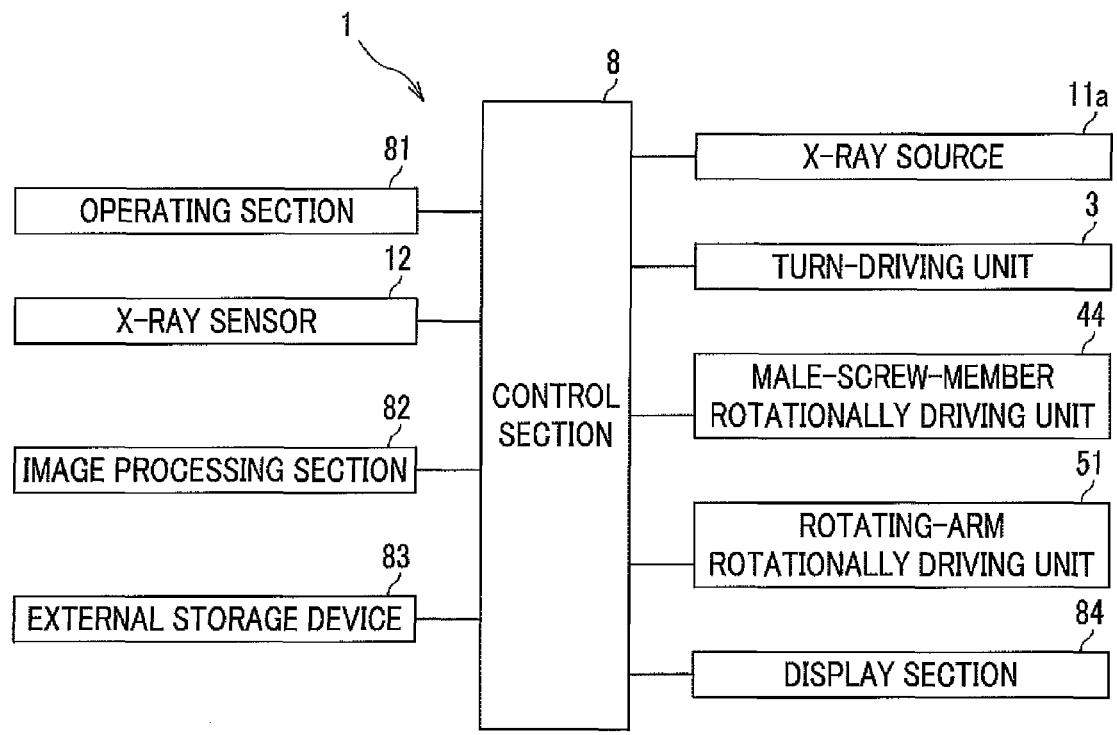
FIG. 3 is a block diagram showing the configuration of the main control of the X-ray imaging device.

FIG. 3 is a block diagram showing the configuration of the main control of the X-ray imaging device 1.

As shown in FIG. 3, the X-ray imaging device 1 is provided with a control section 8 for performing integral control of the entire X-ray imaging device 1. For example, the control section 8 performs control of the operation of X-ray imaging of the subject K. That is, the control section 8 controls the irradiation operation of the X-ray source 11a, and executes detection of X-ray flux L (see FIG. 1) passing through the subject K by the X-ray sensor 12. Further, the control section 8 controls the operation of the turn-driving unit 3, the rotating-arm rotationally driving unit 51 (see FIG. 1) of the shifting unit 5 (see FIG. 1), and the male-screw-member rotationally driving unit 44.

In the present embodiment, the control section 8 is configured to control the operation of X-ray imaging of the subject K (see FIG. 1) while simultaneously executing turning of the X-ray source 11a and the X-ray sensor 12 around the subject K and shifting a transmission part of the subject K, through which the X-ray flux L (see FIG. 1) detected by the X-ray sensor 12 passing.

The X-ray imaging device 1 is also provided with an image processing section 82, an external storage device 83, and a display section 84, which are connected to the control section 8. The image processing section 82 performs image processing of image data (projection data) detected and obtained by the X-ray sensor 12, and generates various images such as CT imagers and panorama images. The external storage device 83 is for example a hard disk device or an optical disk device, and can store various images. The display section 84 is for example an LCD (liquid crystal display) and can display various images.

Further, via an operating section 81, it is possible to switch various imaging modes such as CT imaging and panorama imaging, setting of the shift amount for shifting a transmission part of the subject K, through which the X-ray flux L detected by the X-ray sensor 12 passing.

Figure 4:
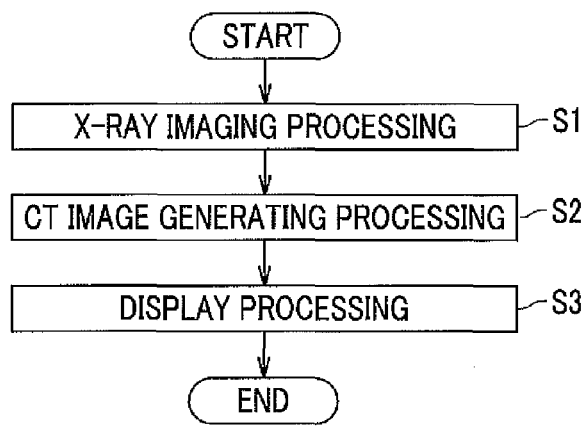
FIG. 4 is a flowchart showing the outline procedure of the operation of CT imaging.

The operation of such configured X-ray imaging device 1 will be described, referring to FIGS. 4 to 11. FIG. 4 is a flowchart showing the outline procedure of the operation of CT imaging. FIGS. 5 to 9 are plan views schematically showing the first to fifth turnings of the X-ray source and the X-ray sensor around the subject.

As shown in FIG. 4, if an operator operates the operating section 81 (see FIG. 1 and FIG. 3), X-ray imaging processing is executed by the X-ray imaging device 1 (step S1). Herein, a case where CT imaging is performed will be described.

In the present embodiment, the control section 8 (see FIG. 3) executes detection of X-ray flux L, which has passed through the subject K, by the X-ray sensor 12, while simultaneously executing: turning of the X-ray source 11a and the X-ray sensor 12 around the subject K by rotating the arcuate movement arm 2 by operation of the turn-driving unit 3 (see FIG. 1); and shifting a transmission part of the subject K, through which the X-ray flux L detected by the X-ray sensor 12 passing, by operation of the shifting unit 5 (see FIG. 1).

Figure 5:
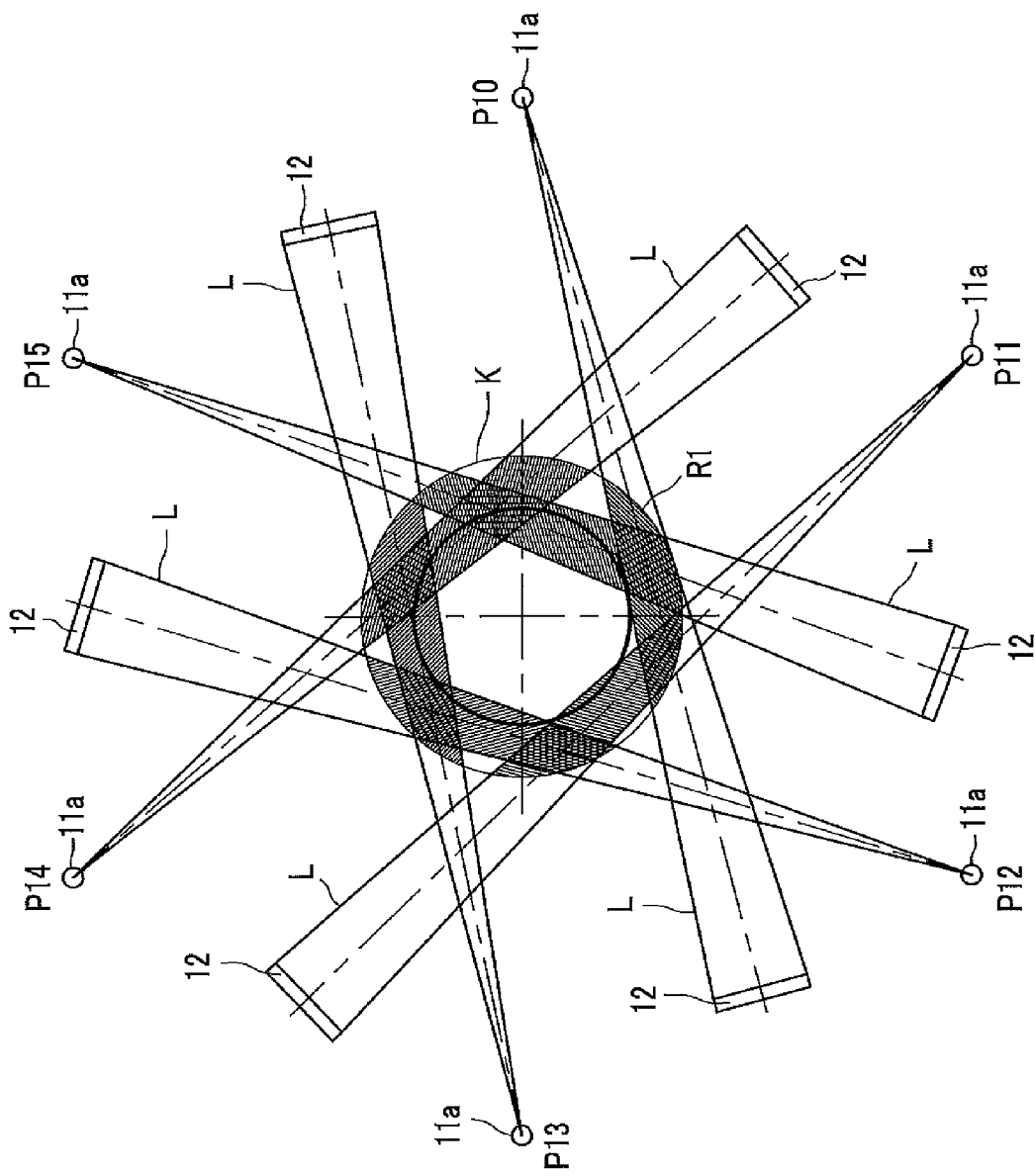
FIG. 5 is a plan view schematically showing the view of the first turning of an X-ray source and an X-ray sensor around a subject.

Concretely, as shown in FIG. 5, first, X-ray flux L projected from the X-ray source 11a located at a position P10 (position at 0 degree), in FIG. 5, in the first turn passes through the first region R1, in FIG. 5, which corresponds to the outermost side (the lowest side in FIG. 5) of the subject K and is detected by the X-ray sensor 12. In the first turn, the X-ray source 11a and the X-ray sensor 12 are turned from this state around the subject K such that the X-ray source 11a rotationally moves by 360 degrees through the positions P11 to P15, and simultaneously, the transmission part of the subject K, through which the X-ray flux L detected by the X-ray sensor 12 passing, is gradually shifted upward from the first region R1 in FIG. 5 to the second region R2 in FIG. 6.

Figure 6:
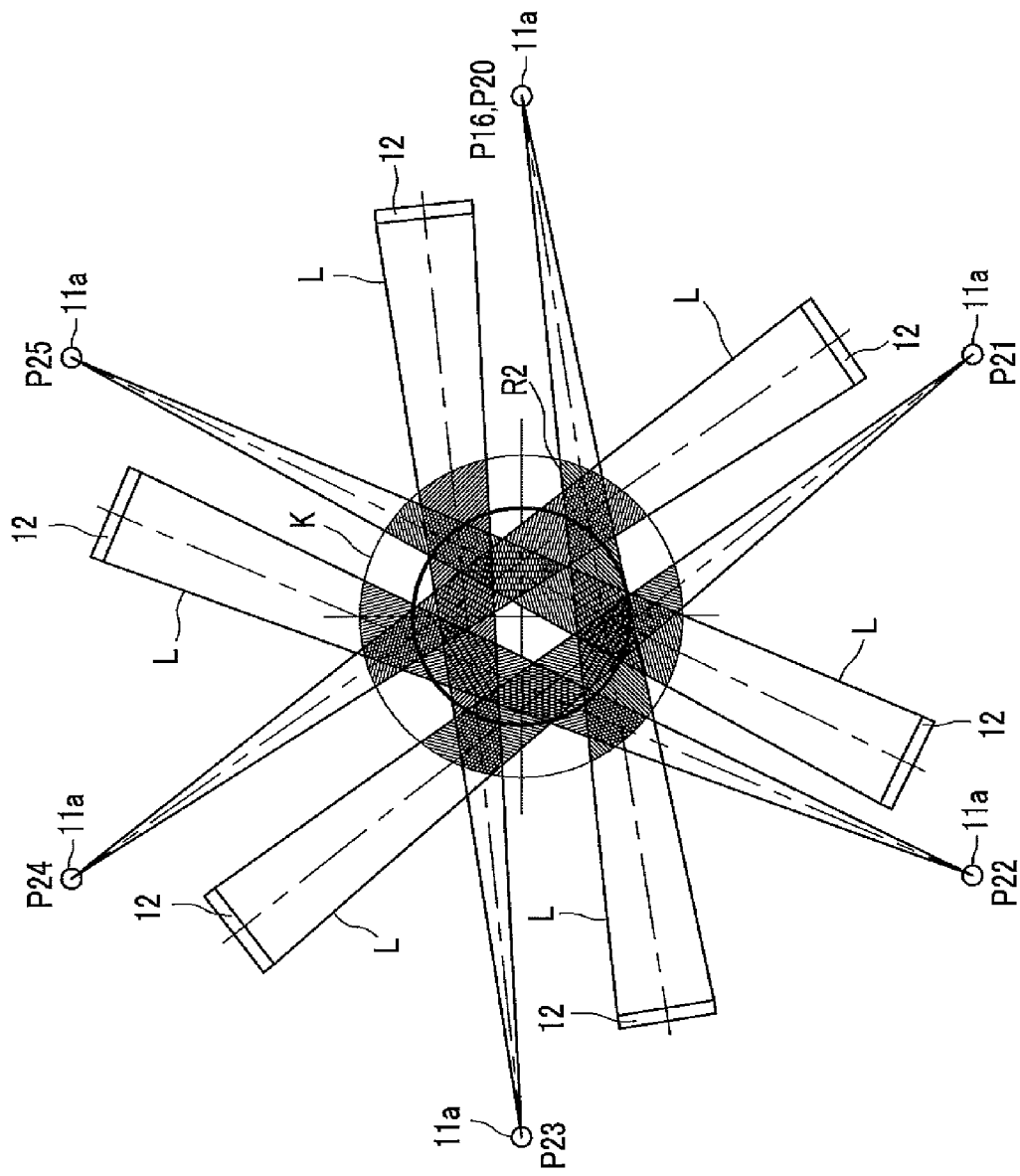
FIG. 6 is a plan view schematically showing the view of the second turning of the X-ray source and the X-ray sensor around the subject.
Figure 7:
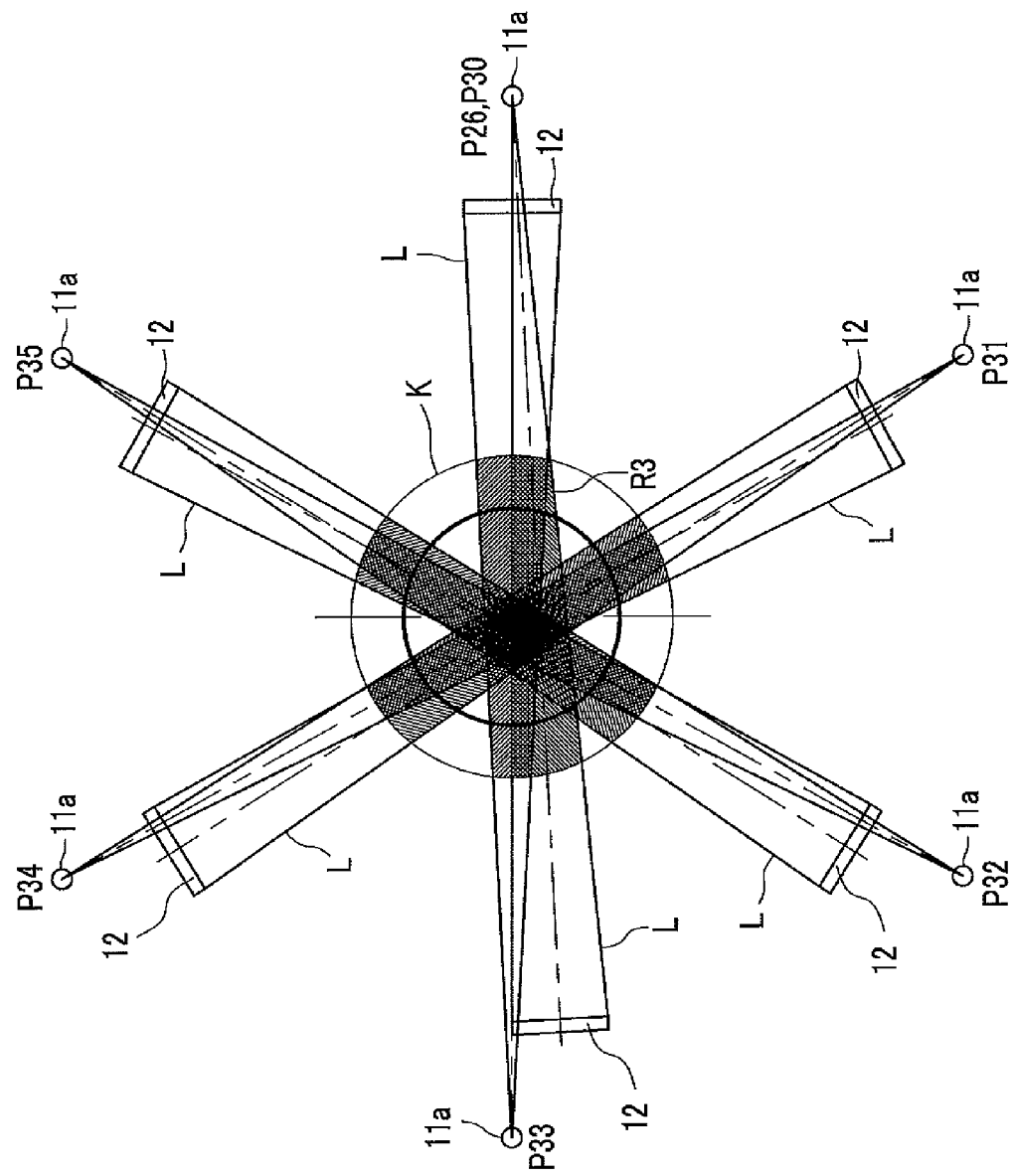
FIG. 7 is a plan view schematically showing the view of the third turning of the X-ray source and the X-ray sensor around the subject.
Figure 8:
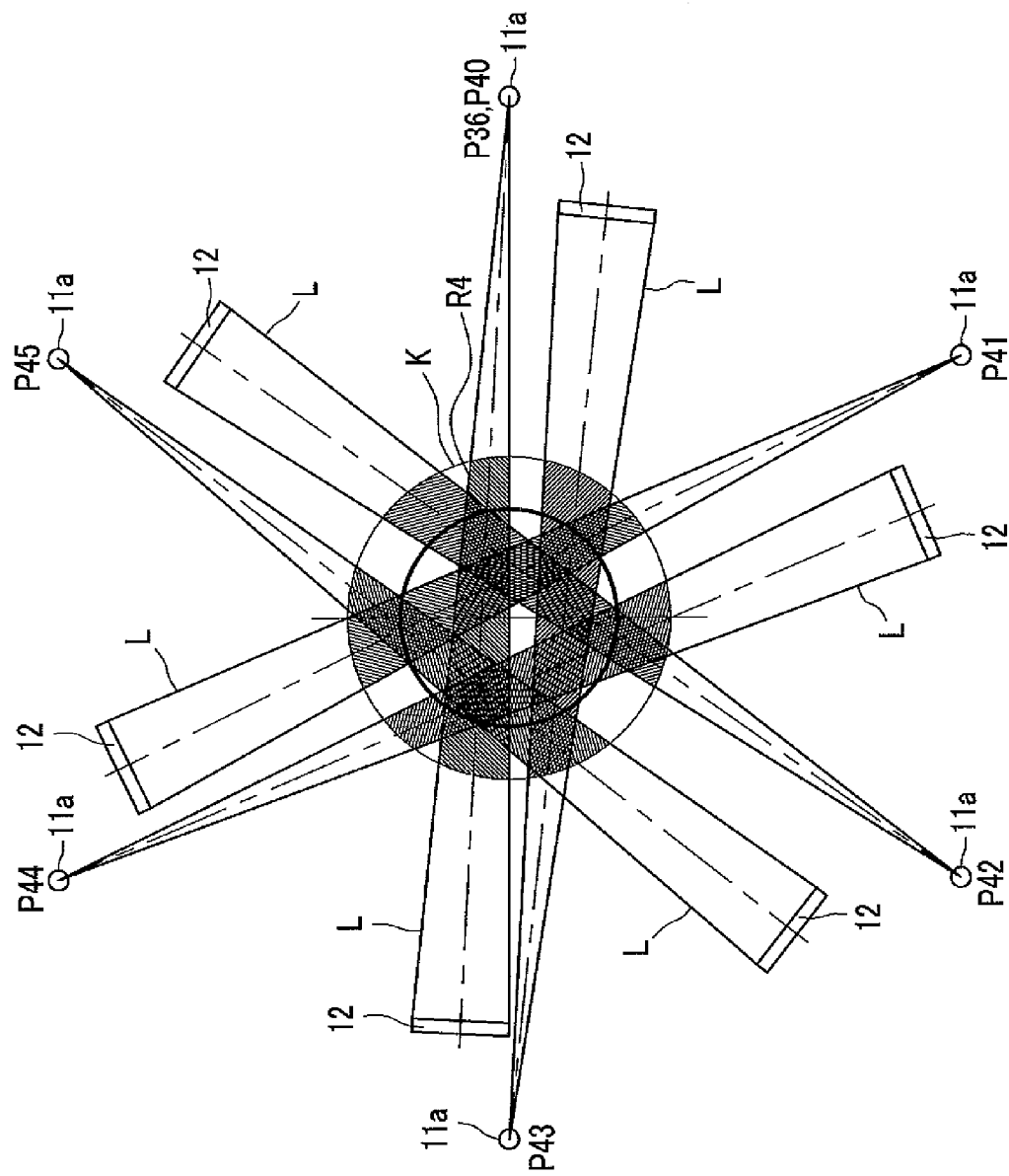
FIG. 8 is a plan view schematically showing the view of the fourth turning of the X-ray source and the X-ray sensor around the subject.
Figure 9:
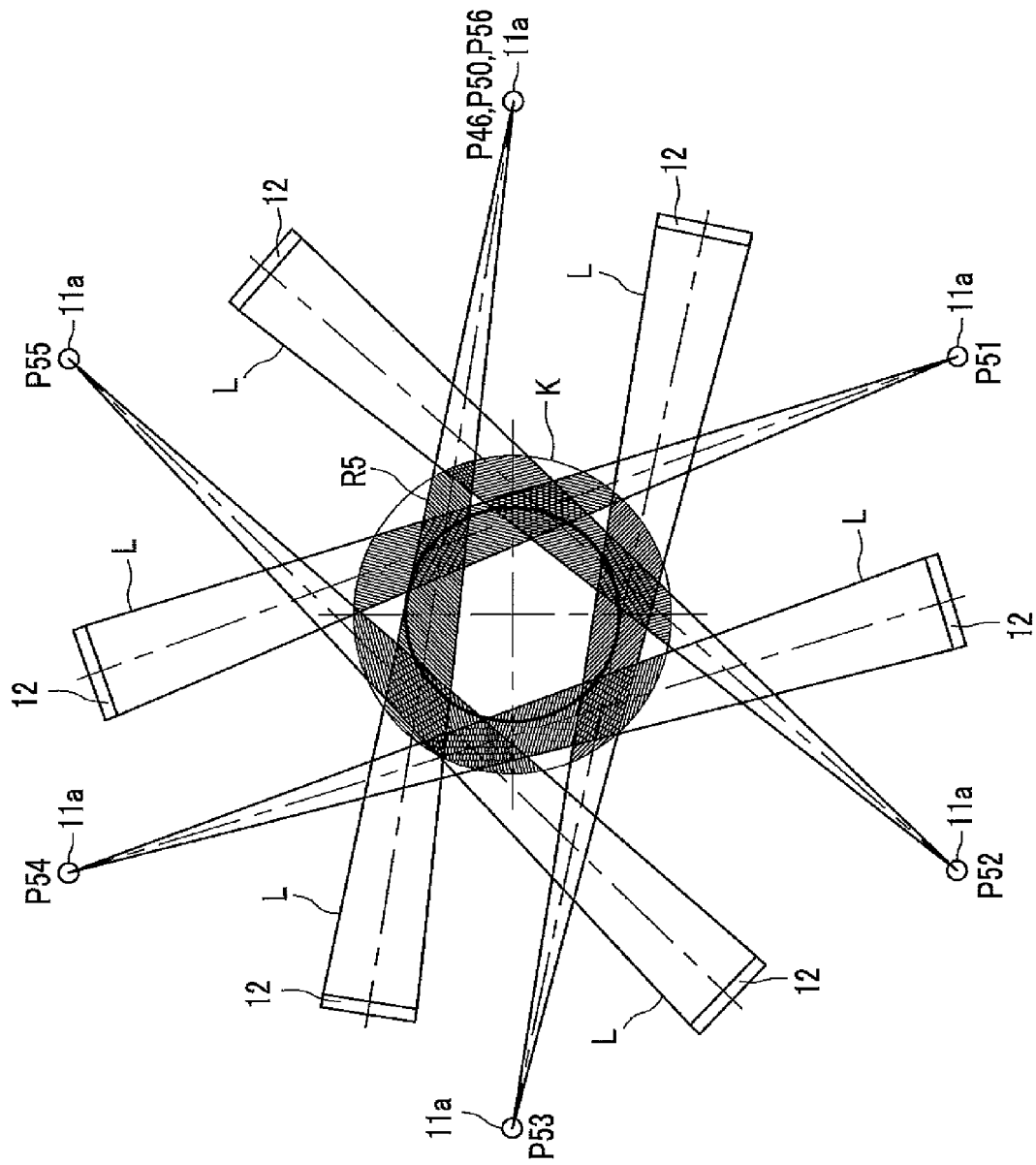
FIG. 9 is a plan view schematically showing the view of the fifth turning of the X-ray source and the X-ray sensor around the subject.

Likewise, in the second turning, as shown in FIG. 6, the X-ray source 11a located at the position P20 (0 degree position) in FIG. 6 rotationally moves by 360 degrees to the position P26 (see FIG. 7) through the positions P21 to P25, and simultaneously, the transmission part of the subject K, through which the X-ray flux L detected by the X-ray sensor 12 passing, is gradually shifted upward from the second region R2 in FIG. 6 to the third region R3 in FIG. 7. In the third turning, as shown in FIG. 7, the X-ray source 11a located at the position P30 (0 degree position) in FIG. 7 rotationally moves by 360 degrees to the position P36 through the positions P31 to P35, and simultaneously, the transmission part of the subject K, through which the X-ray flux L detected by the X-ray sensor 12 passing, is gradually shifted upward from the third region R3 in FIG. 7 to the fourth region R4 in FIG. 8. In the fourth turning, as shown in FIG. 8, the X-ray source 11a located at the position P40 (0 degree position) in FIG. 8 rotationally moves by 360 degrees to the position P46 (see FIG. 9) through the positions P41 to P45, and simultaneously, the transmission part of the subject K, through which the X-ray flux L detected by the X-ray sensor 12 passing, is gradually shifted upward from the fourth region R4 in FIG. 7 to the fifth region R5 in FIG. 9. In the fifth turning, as shown in FIG. 9, the X-ray source 11a located at the position P50 (0 degree position) in FIG. 9 rotationally moves by 360 degrees to the position P56 through the positions P51 to P55, and simultaneously, the transmission part of the subject K, through which the X-ray flux L detected by the X-ray sensor 12 passing, is gradually shifted upper than the fifth region R5 in FIG. 9. Incidentally, in FIG. 9, the transmission part at the position P56 is not shown.

Figure 10:
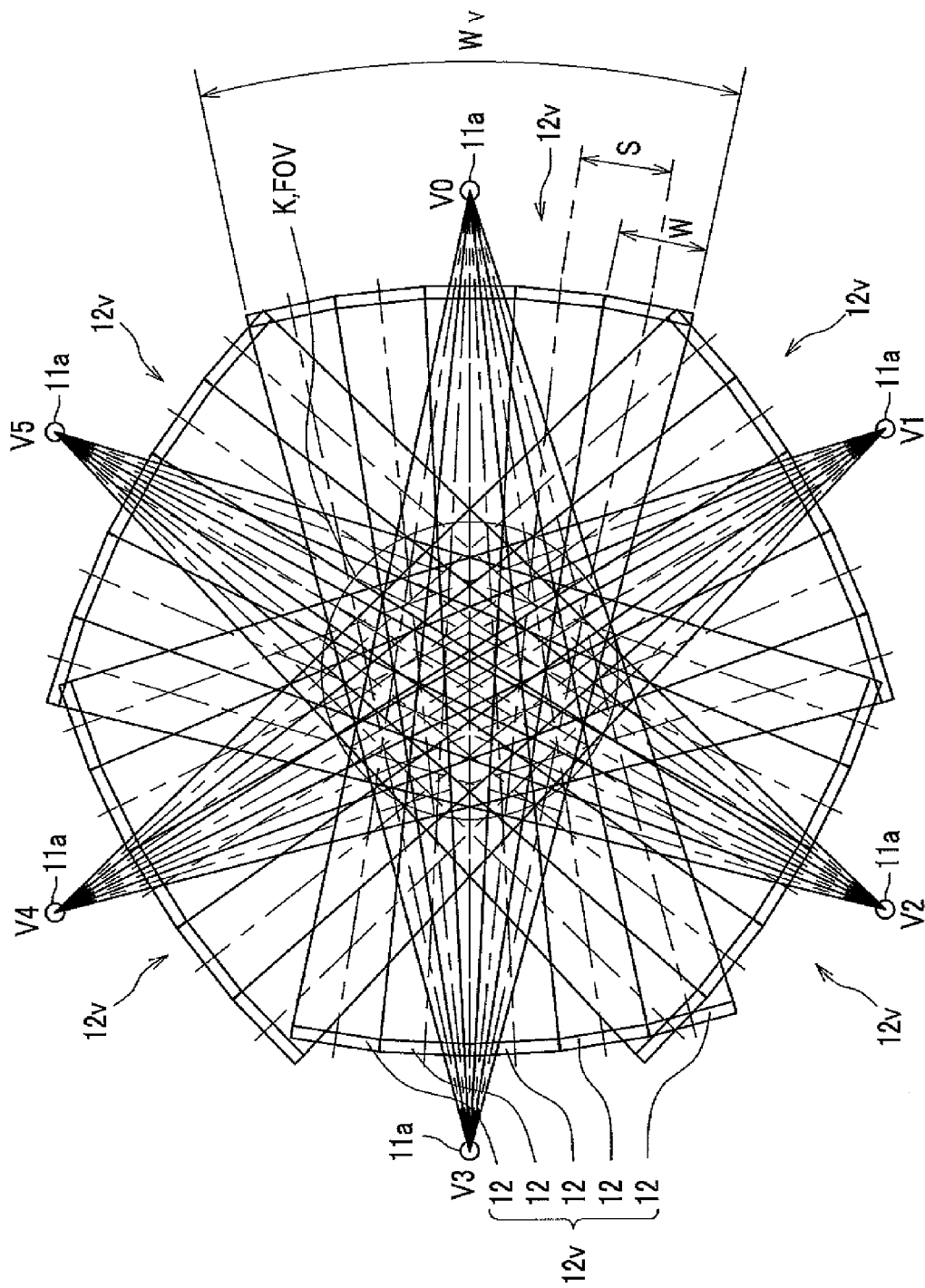
FIG. 10 is a plan view of superposition of FIGS. 5-9.
Figure 11:
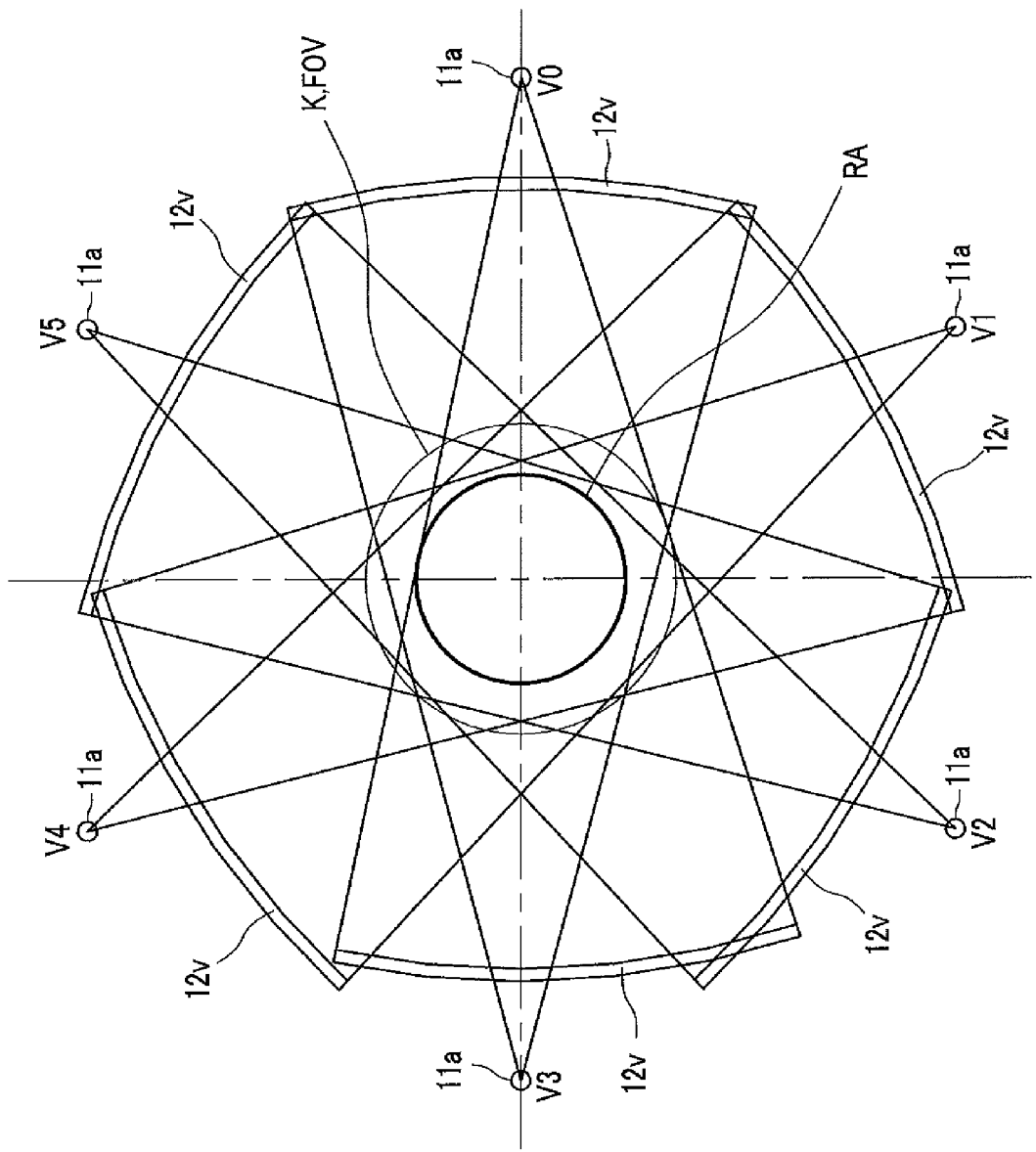
FIG. 11 is a plan view for illustration of a reconstructed image obtaining region where a reconstructed image can be obtained.

FIG. 10 is a plan view of superposition of FIGS. 5-9. FIG. 11 is a plan view for illustration of the reconstructed image obtaining region where a reconstructed image can be obtained.

As shown in FIG. 10, it is proved that, for the same angular position (positions V0 to V5) in the respective turnings, the X-ray source 11a is located at the same position, and the position of the X-ray sensor 12 arcuately moves, in other words, shifts in every turning with the position of the X-ray source 11a as the center. That is, FIG. 10 corresponds to a plan view schematically showing the view of a case of turning a virtual X-ray sensor 12v once around the subject K, the virtual X-ray sensor 12v being in a wide range virtually formed by the shift of the X-ray sensor 12. In FIG. 10, the region of the subject K shows FOV (field of view).

Further, in the present embodiment, the control section 8 controls the operation of the turn-driving unit 3 and the shifting unit 5 such that neighboring transmission parts, through which the X-ray flux L passing, contact with each other at both time points before and after the arcuate movement arm 2 makes one rotation through the turning arm 32. Herein, the shift amount S of the X-ray sensor 12 made by one rotation of the arcuate movement arm 2 is almost equal to the width (effective width) W of the X-ray sensor 12. In the example in FIG. 10, while the X-ray sensor 12 is shifted, the arcuate movement arm 2 is rotated in five times, which is the number of rotations computed as (the width Wv of the virtual X-ray sensor 12v)÷(the width W of the X-ray sensor 12)=5 times. By such an arrangement, image data (projection data) necessary for generation of CT images can be effectively obtained, which enables ensuring image quality and a further improvement of the imaging efficiency.

Incidentally, in the present embodiment, during turning of the X-ray source 11a and the X-ray sensor 12 around the subject K, the transmission part of the subject K, through which the X-ray flux L detected by the X-ray sensor 12 passing, shifts. Consequently, in the example shown in FIG. 11, in the region corresponding to the width of the X-ray sensor 12 at the outer circumferential portion of the FOV, it is not possible to obtain image data (projection data) from all directions and it is difficult to generate reconstructed image such as CT images. Accordingly, the reconstructed image obtaining region RA (see FIG. 11) is a region formed by removing the outer circumferential portion corresponding to the width of the X-ray sensor 12 from the FOV.

Returning to step S2 in FIG. 4, when the image data (projection data) obtained by CT imaging is transmitted to the image processing section 82, the control section 8 controls the image processing section 82 to perform certain processing on the image data (projection data) and thereby generate a CT image.

Subsequently, the control section 8 controls the display section 84 to display the generated CT image (step S3). Further, the generated CT image can be stored in the external storage device 83, as necessary.

In an embodiment as described above, by shifting the transmission part of the subject K, through which the X-ray flux L detected by the X-ray sensor 12 passing, the X-ray sensor 12 can function as a two dimensional X-ray imaging unit for a virtual wide range in a range corresponding to the shifting of the transmission part. In such a manner, using for example an inexpensive X-ray sensor 12 having a detection area in a comparatively narrow range, CT images can be obtained, which contribute to reduction in cost.

While simultaneously executing turning of the X-ray source 11a and the X-ray sensor 12 around the subject K and shifting of the transmission part of the subject K, through which the X-ray flux L detected by the X-ray sensor 12 passing, detection of the X-ray flux L passing through the subject K is executed, and it is thereby possible to reduce temporary stop and restart of moved members such as the X-ray sensor 12. As a result, as it is possible to reduce decrease in the speed caused by operation of temporal stop and restart of the moved members from the start to the end of X-ray imaging, the total imaging time becomes short, and the imaging operation efficiency is improved. Further, as it is possible to decrease the acceleration and deceleration acting on the moved members, the inertia force based on the acceleration or deceleration can be decreased so that the vibration of the moved members caused by the inertia force can be decreased and the durability of the moved members can be improved.

That is, by using an X-ray sensor 12 having a detection area in comparatively narrow range, it is possible to reduce the cost, and also provide an X-ray imaging device 1 that enables improvement of imaging operation efficiency and reduction in vibration of moved members such as the X-ray sensor 12.

Further, in the present embodiment, the X-ray source 11a and the X-ray sensor 12 are arranged at the arcuate movement arm 2, which is a support member, and the arcuate movement arm 2 is axially supported around the arcuate movement central axis C2 arranged at the turning arm 32. Thus, the X-ray source 11a and the X-ray sensor 12 arranged at the arcuate movement arm 2 can be turned around the subject K by the turn-driving unit 3 through the turning arm 32. Further, by rotating the arcuate movement arm 2 by arcuate movement unit as the shifting unit 5, the X-ray sensor 12 can be arcuately moved around the arcuate movement central axis C2, and the transmission part of the subject K, through which the X-ray flux L passing, can be thereby shifted. Accordingly, by detecting the X-ray flux L passing through the subject K while arcuate movement the X-ray sensor 12 by arcuate movement unit, the X-ray sensor 12 can function as a two dimensional imaging unit with a virtual wide range in a range of the arcuate movement.

Second Embodiment

Figure 12:
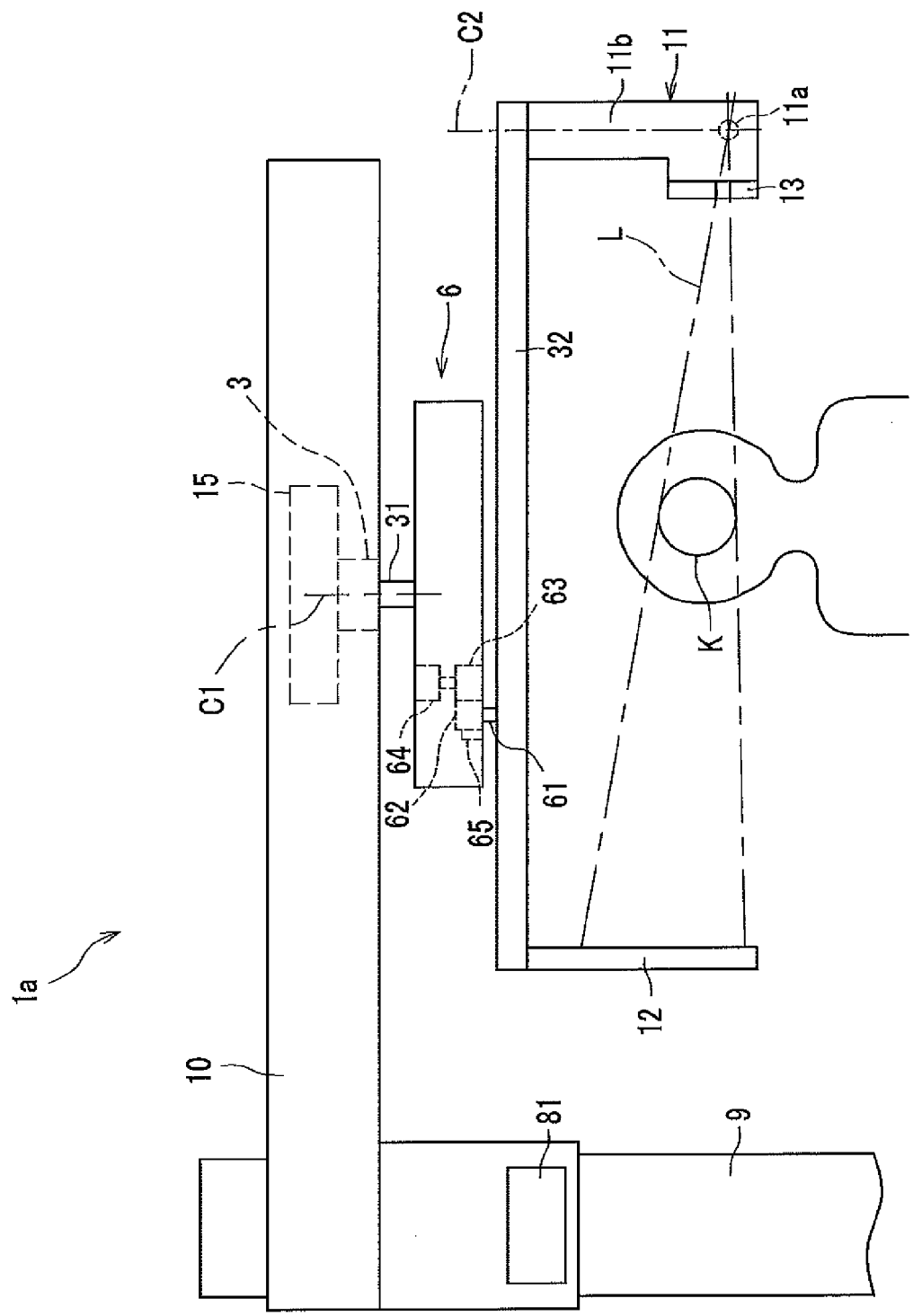
FIG. 12 is a side view schematically showing the outline configuration of an X-ray imaging device in a second embodiment according to the present invention.
Figure 13:
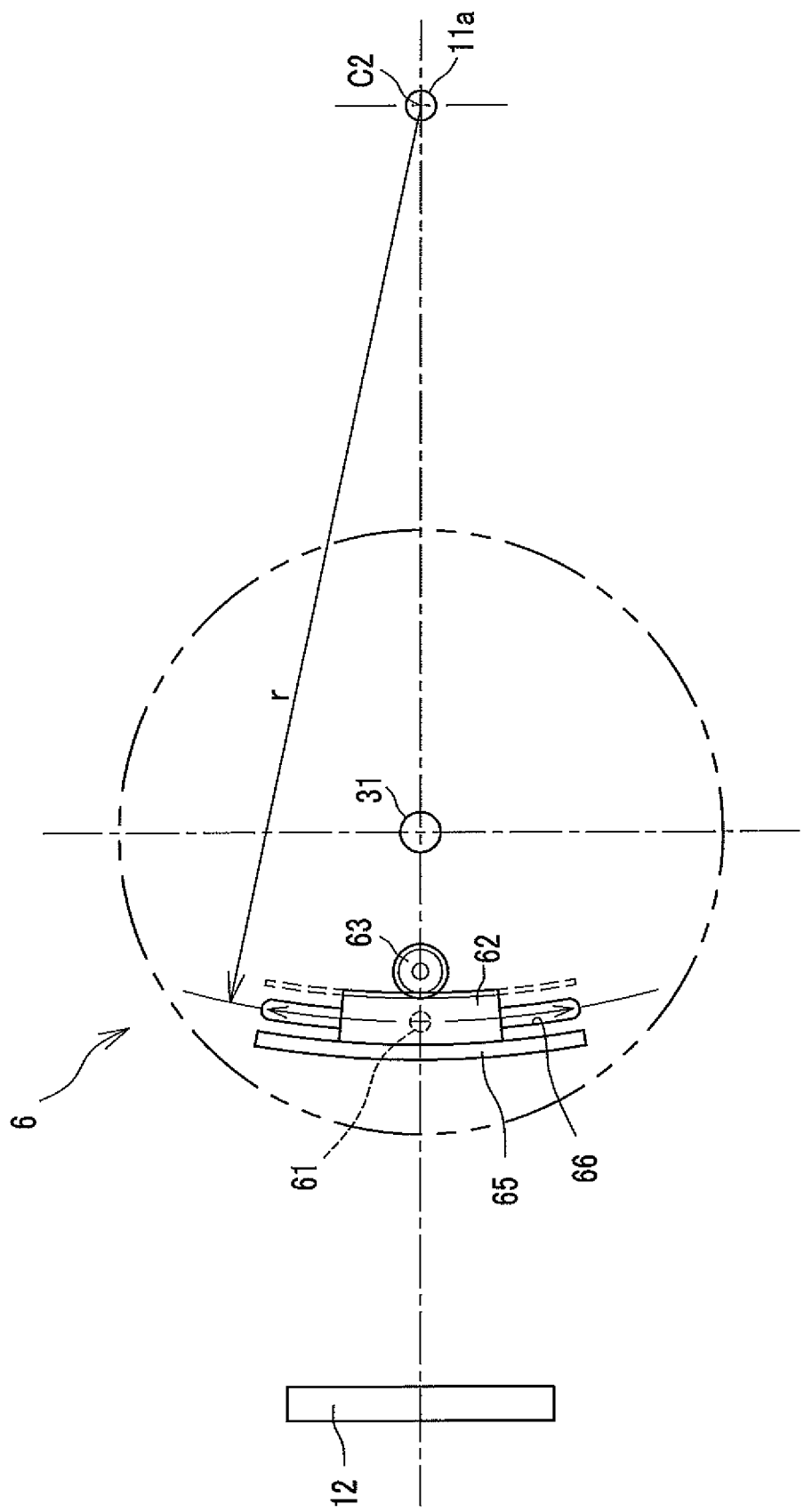
FIG. 13 is a plan view schematically showing the periphery of a shifting unit in the second embodiment.
Figure 14:
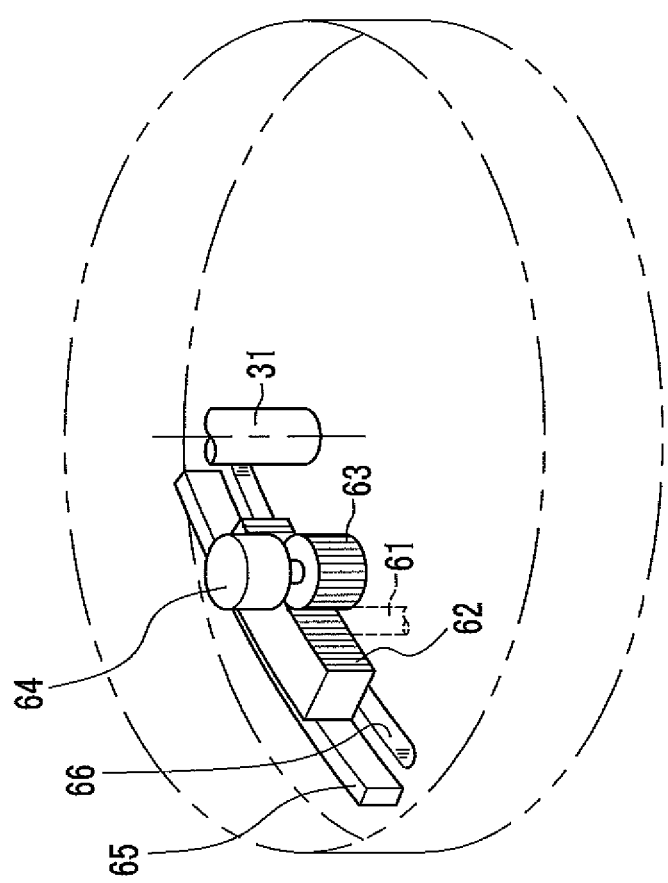
FIG. 14 is a perspective view schematically showing the periphery of the shifting unit in the second embodiment.

FIG. 12 is a side view schematically showing the outline configuration of an X-ray imaging device 1a in a second embodiment according to the present invention. FIG. 13 is a plan view schematically showing the periphery of a shifting unit in the second embodiment. FIG. 14 is a perspective view schematically showing the periphery of the shifting unit in the second embodiment. The X-ray imaging device 1a in the second embodiment will be described on points different from the above-described X-ray imaging device 1 in the first embodiment.

As shown in FIG. 12, in the X-ray imaging device 1a in the second embodiment of the present invention, a shifting unit 6 is different from the shifting unit 5 in the first embodiment in that the shifting unit 6 is a turning-center-position circumferential-direction-moving mechanism that moves the turning central position of a turning arm 32 as a support member along the circumferential direction of a circle with a center at a point on a line connecting the X-ray source 11a with the X-ray sensor 12 being herein a point on an arcuate movement central axis C2, which is a vertical shaft going through the X-ray source 11a. Incidentally, in the second embodiment, a turning-center-position horizontally moving mechanism 4 as one in the first embodiment is omitted, however, may be installed.

A turning shaft 31 is fixed to the upper portion of the shifting unit 6, and has a connecting shaft 61 fixed to the upper surface of the turning arm 32.

The shifting unit 6 has a function to move the connecting shaft 61 around the arcuate movement central axis C2 to thereby arcuately move the turning center position of the turning arm 32 as a result. Herein, the turning center position of the turning arm 32 corresponds to the intersection point on the turning arm 32 with the arm turning central axis C1.

As shown in FIGS. 12 to 14, the shifting unit 6 is provided with a slide gear 62 in an arcuate shape to which the connecting shaft 61 is fixed, a pinion gear 63 engaged with the slide gear 62, a pinion gear rotational-driving unit 64 such as a servo motor for rotationally driving the pinion gear 63, and a guide member 65 for guiding the circumferentially directed movement (arcuate movement) of the slide gear 62. Inner teeth are formed inside the slide gear 62, with the arcuate movement central axis C2 as the center. That is, in the shifting unit 6, the pinion gear 63 is rotated by the operation of the pinion gear rotational-driving unit 64, and the gear force moves the slide gear 62 so that the connecting shaft 61 can be shifted along the circumferential direction of a circle with a radius r (see FIG. 14) with the arcuate movement central axis C2 as the center. Incidentally, symbol 66 in FIG. 13 and FIG. 14 represents a guide groove for guiding the movement of the connecting shaft 61.

In the second embodiment, the turning arm 32 as a support member, the turning arm 32 being provided with the X-ray source 11a and the X-ray sensor 12, is turned around the turning center position of the turning arm 32 by the turn-driving unit 3, and the turning center position of the turning arm 32 is moved along the circumferential direction with the arcuate movement central axis C2 as the center by the shifting unit 6, which is a turning-center-position circumferential-direction-moving mechanism. Thus, the X-ray sensor 12 is arcuately moved around the arcuate movement central axis C2, and the transmission part of the subject K, through which the X-ray flux L passing, can be shifted. Accordingly, by detecting X-ray flux L passing through the subject K while arcuate movement the X-ray sensor 12 by the shifting unit 6, which is a turning-center-position circumferential-direction-moving mechanism, the X-ray sensor 12 can function as a two dimensional imaging unit in a virtual wide range in a range of the arcuate movement.

Accordingly, also in the second embodiment, operation and advantages similar to those in the above-described first embodiment can be obtained.

Third Embodiment

Figure 15:
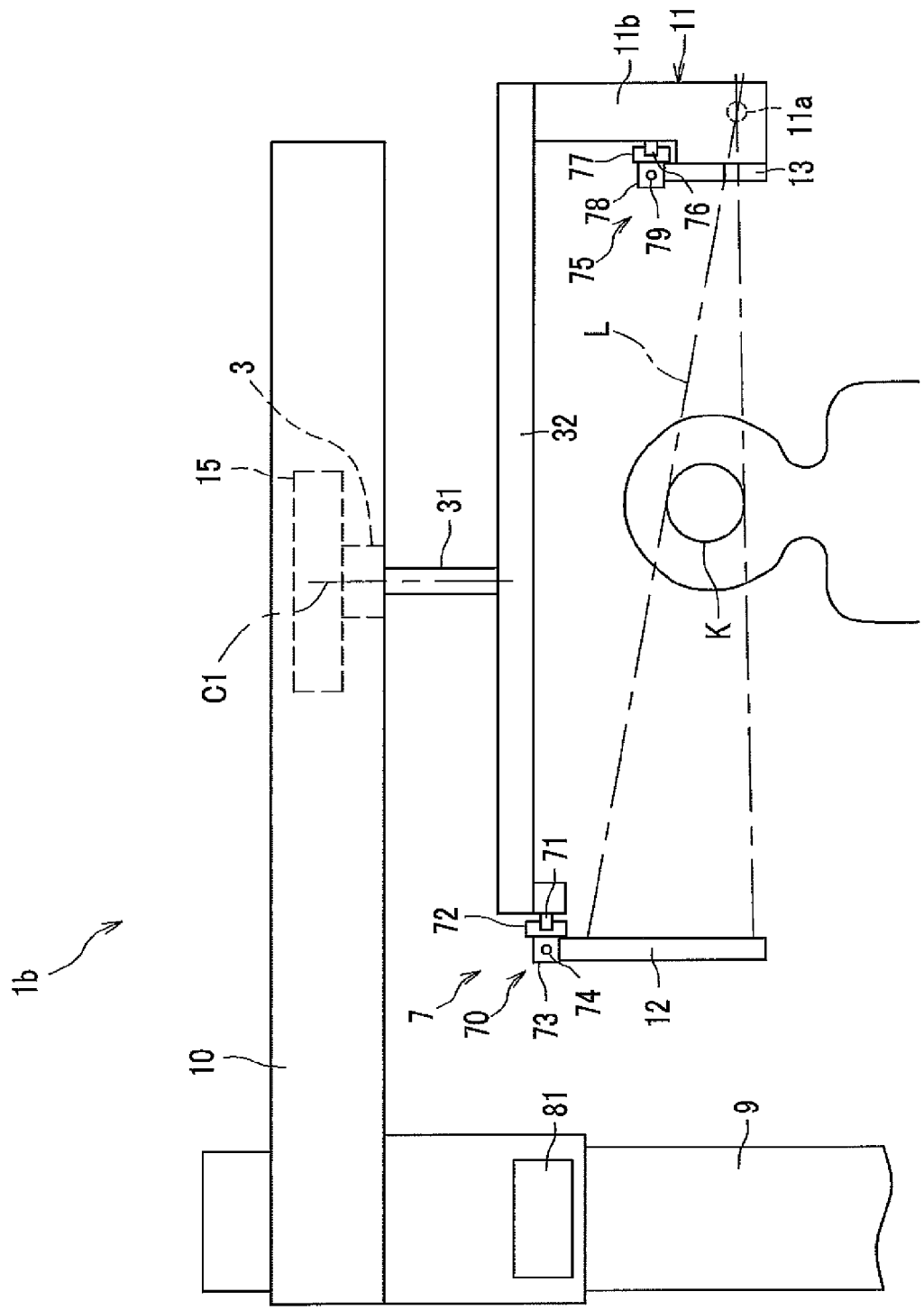
FIG. 15 is a side view schematically showing the outline configuration of an X-ray imaging device in a third embodiment according to the present invention.

FIG. 15 is a side view schematically showing the outline configuration of an X-ray imaging device 1b in a third embodiment according to the present invention. In the following, the X-ray imaging device 1b in the third embodiment will be described on points different from the above-described X-ray imaging device 1 in the first embodiment.

As shown in FIG. 15, in the X-ray imaging device 1b in the third embodiment according to the present invention, a shifting unit 7 is different from the shifting unit 5 in the first embodiment in that the shifting unit 7 is a linear moving unit that is provided at a turning arm 32 as a support member and linearly moves the X-ray sensor 12. Incidentally, in the third embodiment, a turning-center-position horizontally moving mechanism 4 as one in the first embodiment is omitted, however, may be installed.

While, in the above-described first and second embodiments, the X-ray sensor 12 is arcuately moved around the arcuate movement central axis C2, the third embodiment corresponds to a case that the arcuate movement central axis C2 (see FIG. 1 and FIG. 12) is set at a distance extremely far from the subject K.

The shifting unit 7, which is a linearly moving unit for linearly moving, is provided with a linearly moving unit 70 for linearly moving the X-ray sensor 12, and a linearly moving unit 75 for linearly moving a slit 13 for restricting the range of X-ray flux L projected from the X-ray source 11a. The linearly moving unit 70 is arranged at the turning arm 32. The linearly moving unit 75 is arranged at the turning arm 32 through a support member 11b, however, may be arranged directly at the turning arm 32.

The linearly moving unit 70 is provided with a guide rail 71 arranged along the direction of linear moving, a holder 72 reciprocally movably attached along the guide rail 71, a nut section 73 fixed to the holder 72, a male screw member 74 screw-engaged with the nut section 73, and a male-screw-member rotationally driving unit not shown such as a servo motor that rotationally drives the male screw member 74.

Further, the linearly moving unit 75 for linearly moving the slit 13 is likewise provided with a guide rail 76, a holder 77, a nut section 78, a male screw member 79, and a male-screw-member rotationally driving unit not shown such as a servo motor that rotationally drives the male screw member 79. The linearly moving unit 70 and the linearly moving unit 75 are controlled in order to move in synchronization with each other.

In the third embodiment, the X-ray sensor 12 can be linearly moved by the shifting unit 7, which is a unit for linearly moving, and the transmission part of the subject K, through which the X-ray flux L passing, can be thereby shifted. Accordingly, by detecting X-ray flux L passing through the subject K while linearly moving the X-ray sensor 12 by the shifting unit 7, which is a unit for linearly moving, the X-ray sensor 12 can function as a two dimensional imaging unit in a virtual wide range in a range of the linear movement.

Accordingly, also in the third embodiment, operation and advantages similar to those in the above-described first embodiment can be obtained.

The present invention has been described above, based on embodiments, however, the invention is not limited to the structures described in the above-described embodiments, and modifications and changes of the structures can be made, as appropriate, in a range without departing from the spirit of the invention, including combination or selection, as appropriate, of the structures described in the above-described embodiments.

For example, in the above-described embodiments, the shift amount S by which the X-ray sensor 12 shifts when the arcuate movement arm 2 makes one rotation was set in order to be substantially equal to the width (effective width) W of the X-ray sensor 12, however, the invention is not limited thereto. The shift amount S can be set, as appropriate, depending on a required resolution of a CT image or the like. For example, the shift amount S may be set in order to form a gap between neighboring transmission parts, through which the X-ray flux L passing, or may be set such that the neighboring transmission parts partially overlap with each other, at both time points before and after the arcuate movement arm 2 make one rotation. Further, the shift amount S can also be set such that the shift amount S, by which the X-ray sensor 12 shifts when the arcuate movement arm 2 makes for example a half rotation, is substantially equal to the width (effective width) W of the X-ray sensor 12.

Further, in the above-described embodiments, the number of times of turning the arcuate movement arm 2 in X-ray imaging was set to for example five times, however, arrangement may be made such that the number of times can be set in order to match the necessity via the operating section 81.

Further, the shifting units 5 to 7 are examples of shifting units for shifting the transmission part of the subject K, through which the X-ray flux L detected by the X-ray sensor 12 passing, and shifting units are not limited to the structures in the above-described first to third embodiments. For example, in the second embodiment, the X-ray sensor 12 is arcuately moved around the X-ray source 11a, however, arrangement may be made such that the X-ray source 11a is arcuately moved around the X-ray sensor 12. In this case also, it is possible to shift the transmission part of the subject K, through which the X-ray flux L passing. Further, the shifting unit 7 in the third embodiment is not particularly limited to the structure described above, and it is also possible to implement a unit for linearly moving by adopting a straight rack instead of the slide gear 62 in an arcuate shape in the second embodiment shown in FIGS. 12 to 14.

Still further, in the first and second embodiments, the arcuate movement central axis C2 was arranged at the X-ray source 11a, however, without being limited thereto, the arcuate movement central axis C2 may be arranged on a line connecting the subject K with the X-ray sensor 12. Further, in the present embodiment, the slit 13 for restricting the range of X-ray flux L was arranged, however, without being limited thereto, the invention can be carried out even without providing the slit 13.

Yet further, in the above-described embodiments, CT image generating processing (step S2) is executed after the X-ray imaging processing (step S1) is completed, however, the invention is not limited thereto, and generation of CT images may be sequentially executed from a region in which image reconstructing has become possible during X-ray imaging processing. By such an arrangement, the total time of CT imaging operation can be shortened, An X-ray imaging device may also be used for medical care other than dental care. Further, the object of imaging may be other than human being, and accordingly, an X-ray imaging device may be used for testing of a thing.

DESCRIPTION OF REFERENCE SYMBOLS

1, 1a, 1b: X-ray imaging device
2: arcuate movement arm (support member)
3: turn-driving unit
4: turning-center-position horizontally moving mechanism
5-7: shifting unit
8: control section
11a: X-ray source
12: X-ray sensor
13: slit
32: turning arm (support member)
70: linearly moving unit
C1: arm turning central axis
C2: arcuate movement central axis
K: subject
L: X-ray flux
R1-R5: region of transmission part

We claim:

1. An X-ray imaging device, comprising:
an X-ray source for irradiating a subject with X-ray flux;
an X-ray imaging unit for detecting the X-ray flux passing through the subject;
a support member for supporting the X-ray source and the X-ray imaging unit;
a turn-driving unit for turning the X-ray source and the X-ray imaging unit around the subject by rotating the support member;
a shifting unit for shifting a transmission part of the subject, through which the X-ray flux detected by the X-ray imaging unit passing; and
a control section for controlling operation of the turn-driving unit and the shifting unit,
wherein the control section executes detection of the X-ray flux passing through the subject by the X-ray imaging unit, while simultaneously executing turning of the X-ray source and the X-ray imaging unit around the subject by rotating the support member by operating the turn-driving unit, and shifting the transmission part of the subject, through which the X-ray flux detected by the X-ray imaging unit passing, by operating the shifting unit.

2. The X-ray imaging device according to claim 1, wherein the control section controls operation of the turn-driving unit and the shifting unit such that neighboring transmission parts, through which the X-ray flux passing, contact with each other at both time points before and after the support member is rotated one time.

3. The X-ray imaging device according to claim 1, further comprising:
a turning-center-position horizontally moving mechanism for horizontally moving a turning center position of the support member in a direction along a line connecting the X-ray source with the X-ray imaging unit.

4. The X-ray imaging device according to claim 2, further comprising:
a turning-center-position horizontally moving mechanism for horizontally moving a turning center position of the support member in a direction along a line connecting the X-ray source with the X-ray imaging unit.

5. The X-ray imaging device according to claim 1, wherein a slit for restricting a range of X-ray projected from the X-ray source is arranged in order to face the X-ray imaging unit across the subject.

6. The X-ray imaging device according to claim 2, wherein a slit for restricting a range of X-ray projected from the X-ray source is arranged in order to face the X-ray imaging unit across the subject.

7. The X-ray imaging device according to claim 3, wherein a slit for restricting a range of X-ray projected from the X-ray source is arranged in order to face the X-ray imaging unit across the subject.

8. The X-ray imaging device according to claim 4, wherein a slit for restricting a range of X-ray projected from the X-ray source is arranged in order to face the X-ray imaging unit across the subject.

9. The X-ray imaging device according to claim 1,
wherein the shifting unit is an arcuate movement unit for arcuate moving the X-ray imaging unit around the subject in order to rotate the X-ray imaging unit around an arcuate movement central axis arranged on a line connecting the subject with the X-ray imaging unit,
wherein the support member comprises an arcuate movement arm that is axially supported around the arcuate movement central axis arranged for a turning arm turned by the turn-driving unit,
wherein the arcuate movement unit that arcuately moves the arcuate movement arm is arranged under the turning arm,
wherein the X-ray source and the X-ray imaging unit are rotated around the subject by rotating the arcuate movement arm by turning the arcuate movement arm by the turn-driving unit, and
wherein the X-ray imaging unit is arcuately moved around the subject by rotating the arcuate movement arm by the arcuate movement unit.

10. The X-ray imaging device according to claim 9, wherein the arcuate movement central axis is provided at a position where the X-ray source is arranged.

11. The X-ray imaging device according to claim 1, wherein the shifting unit is a turning-center-position circumferential-direction-moving mechanism for moving a turning-center position of the support member along a circumferential direction of a circle having a center at a point on a line connecting the X-ray source with the X-ray imaging unit.

12. The X-ray imaging device according to claim 1, wherein the shifting unit is a linearly moving unit arranged at the support member to linearly move the X-ray imaging unit.

* * * * *